United States Patent
Chen et al.

(10) Patent No.: US 10,048,242 B2
(45) Date of Patent: Aug. 14, 2018

(54) INLINE WATER CONTAMINANT DETECTOR

(71) Applicant: ECOMO INC., Sunnyvale, CA (US)

(72) Inventors: Gang Chen, Coraopolis, PA (US); Zhiqiang Li, Herndon, VA (US)

(73) Assignee: Shenzhen Yimu Technology Co., Ltd., Shenzhen (CN)

( * ) Notice: Subject to any disclaimer, the term of this patent is extended or adjusted under 35 U.S.C. 154(b) by 0 days.

(21) Appl. No.: 15/174,809

(22) Filed: Jun. 6, 2016

(65) Prior Publication Data

US 2016/0356713 A1 Dec. 8, 2016

Related U.S. Application Data (60) Provisional application No. 62/172,119, filed on Jun. 7, 2015.

(51) Int. Cl.
*G01N 21/59* (2006.01)
*G01N 33/18* (2006.01)
(Continued)

(52) U.S. Cl.
CPC .............. *G01N 33/18* (2013.01); *B01D 29/60* (2013.01); *B01D 29/96* (2013.01); *B01D 35/143* (2013.01); *C02F 1/003* (2013.01); *C02F 1/283* (2013.01); *G01N 21/33* (2013.01); *G01N 21/59* (2013.01); *G01N 21/85* (2013.01); *G01N 33/1826* (2013.01); *C02F 2209/06* (2013.01); *C02F 2209/10* (2013.01); *C02F 2209/20* (2013.01); *C02F 2307/06* (2013.01);
(Continued)

(58) Field of Classification Search
CPC ........ G01N 21/59; G01N 33/18; C02F 1/325; C02F 1/32; C02F 2201/3222; A61L 2/10; A61L 2/0047
See application file for complete search history.

(56) References Cited

U.S. PATENT DOCUMENTS 3,948,772 A * 4/1976 Ellner ............... A61L 2/10
                210/101
4,676,896 A * 6/1987 Norton ............... C02F 1/325
                210/192

(Continued)

OTHER PUBLICATIONS

Cho et al., Using UV254 as a TOC Surrogate for Intentional Contaminant Detection in Drinking Water Distribution Systems, 8th Annual Water Distribution Systems Analysis Symposi.

*Primary Examiner* — Marcus Taningco
(74) *Attorney, Agent, or Firm* — Chan Hubbard PLLC; Keala Chan (57) ABSTRACT

A device installable into a tap to detect the presence of one or more types of contaminants in the tap water. When the tap is operated, a sample chamber fills with the tap water, such that one or more electronic receivers are capable of detecting the presence of contaminants. Preferably, at least one of the one or more electronic receivers is a photometric sensor for detecting absorption of ultraviolet (UV) light in the 250 nm to 300 nm range. A UV254 LED can be activated when water fills the sample chamber, and a measurement circuit calculates Total Organic Carbon (TOC) by correlation with UV254 absorbance. The device can transmit contamination data, including, but not limited to TOC levels, to a remote apparatus for remote monitoring of the tap water.

9 Claims, 8 Drawing Sheets

(51) Int. Cl.
*G01N 21/33* (2006.01)
*B01D 29/60* (2006.01)
*B01D 29/96* (2006.01)
*B01D 35/143* (2006.01)
*C02F 1/00* (2006.01)
*C02F 1/28* (2006.01)
*G01N 21/85* (2006.01)
*G01N 21/51* (2006.01)

(52) U.S. Cl.
CPC ..... *G01N 21/51* (2013.01); *G01N 2021/8571* (2013.01); *G01N 2201/062* (2013.01); *Y02A 20/206* (2018.01)

(56) References Cited

U.S. PATENT DOCUMENTS

| | | | | |
|---|---|---|---|---|
| 4,943,370 A | * | 7/1990 | Gortowski | B01D 17/0214 210/109 |
| 5,843,309 A | * | 12/1998 | Mancil | C02F 1/325 210/205 |
| 6,178,816 B1 | * | 1/2001 | Katzman | E03B 7/072 285/30 |
| 6,909,101 B2 | * | 6/2005 | Nishioka | C02F 1/325 210/192 |
| 8,650,946 B1 | * | 2/2014 | Feller | G01F 25/0007 73/202.5 |
| 8,957,387 B2 | | 2/2015 | Sexton | |
| 2002/0117631 A1 | * | 8/2002 | Gadgil | A61L 2/10 250/434 |
| 2004/0165185 A1 | * | 8/2004 | Reintjes | G01N 15/0227 356/335 |
| 2005/0218054 A1 | * | 10/2005 | Sakata | A61L 2/18 210/192 |
| 2006/0163169 A1 | * | 7/2006 | Eckhardt | C02F 1/002 210/748.11 |
| 2006/0231780 A1 | * | 10/2006 | Salven | G01N 30/74 250/573 |
| 2009/0025472 A1 | * | 1/2009 | Garvin | G01F 5/00 73/202 |
| 2009/0121165 A1 | * | 5/2009 | Aroussi | G01N 15/0227 250/573 |
| 2016/0280562 A1 | * | 9/2016 | Liao | C02F 1/008 |
| 2016/0289090 A1 | * | 10/2016 | Liao | C02F 1/325 |
| 2016/0340202 A1 | * | 11/2016 | Lautzenheiser | C02F 9/005 |

* cited by examiner

INLINE WATER CONTAMINANT DETECTOR

FIELD OF THE INVENTION

The invention relates to the field of water contaminant detectors.

BACKGROUND OF THE INVENTION

Water safety and purity is a civic necessity of utmost importance. Human health and safety dictates that drinking and other home use water must meet various health and environmental standards. Contaminated equipment or fluids at various sources in the water supply can affect thousands of homes and lives. Sabotage and attacks on the water supply must not only be prevented, but rapidly detected. Consumers feel increasingly insecure about the water in their home taps. Despite water purification by state and local municipalities, many consumers install filtration system in order to purify their water.

Public water utilities and state and local agencies typically perform contaminant detection at water treatment centers, public water supplies and wells, and other central locations in the water distribution system, as well as by grab sampling, in which technicians collect field samples or perform measurements in the field. A common analytic technique for measuring water quality is to determine the level of Total Organic Carbon ("TOC") in the water. TOC can come from decaying organic matter or synthetic sources such as industrial chemicals or fertilizers, and as such is an indicator of water quality.

Typical TOC analyzers are large and expensive devices that are best suited for utilization on-site at central locations in the water supply. Some devices burn the sample in a furnace then analyze remaining $CO_2$, which is directly proportional to the amount of carbon in the sample. More recently, UV254 has been used as a TOC substitute, wherein the amount of UV254 absorbed by the water is known to be proportional to the concentration of organic carbon matter in the water. Devices that use UV254 typically use a large light source with large power requirement, for high accuracy measurement. Furthermore, these instruments use a standing sample of water, to further increase their accuracy.

SUMMARY OF THE INVENTION

The invention is the first affordable, low-power, low-profile device that can be installed directly onto a home faucet or water line, enabling contamination detection in real-time. Instead of relying exclusively on municipal testing for ascertaining water contamination, residents can now test for TOC and other contaminants directly from their own tap. Instead of purchasing water filtration systems and/or bottled water, consumers can now rely upon a device installed on their own tap for integrated detection and filtration.

A device is described that identifies contaminants in a flow of water from the tap. The miniaturization and installability of the device is made possible by the device diverting water from the flow of the tap and into a sampling chamber where turbulence is minimized. One or more receivers disposed in or around the sample chamber collect data from the fluid in the chamber, and the data is transmitted to an integrated circuit for further processing and/or transmittal for display. Minimal turbulence in the sampling chamber, automatic activation, highly efficient integrated circuit, and optional redundant data collection all contribute to the accuracy of the contaminant calculation, and to the ability to build the device to low power specifications.

The preferred embodiment utilizes ultraviolet (UV) light, preferably in the range of 250 nm to 300 nm, the absorption of which correlates to TOC level in the water. A UV254 LED, desirable for its low power requirement, transmits UV254 into the sample chamber for collection by a photometric sensor, the current output of which is input to a TOC algorithm to calculate a TOC measurement. A temperature probe near the LED may further refine the calculation to account for changes in light strength due to temperature fluctuations. The photometric sensor may also receive data from an additional IR (infrared) LED, and the IR absorption can be used to calculate water turbidity and/or refine the accuracy of the TOC measurement. Furthermore, the receiving of data from the IR LED, positioned at an angle such that its light is refracted away from the sensor until the chamber is full, automatically activates the UV254 LED and TOC measurement circuit.

Other embodiments may comprise any combinations of receivers, which are not limited to photometric sensors. For instance, another embodiment may comprise two electrodes within the sample chamber for measuring the sample's electrical conductivity, which is directly proportional to TDS level. TDS, or Total Dissolved Solids, is a measure of the combined inorganic and organic substances in the water, and as such is another useful measure of contamination.

Data from the device may be displayed on the device, or it may be transmitted to a remote display for monitoring by a user. For instance, the preferred embodiment comprises a personal device, such as a smartphone, with an application for displaying a variety of contamination information to the user. This information can include, but is not limited to, the level of each type of contaminant detected in the water, comparisons to recommended safety levels, water filter replacement recommendations, and locations of water contamination events as detected by similar devices installed by other consumers. The application may send and receive data from a server for storage and retrieval of water contamination data. A central repository of water contamination data from the described devices may help governments and municipalities identify and solve problems in the water supply.

DETAILED DESCRIPTION

As noted in the Background, typical water contaminant detectors are large devices that are applied to standing water.

Figure 1:
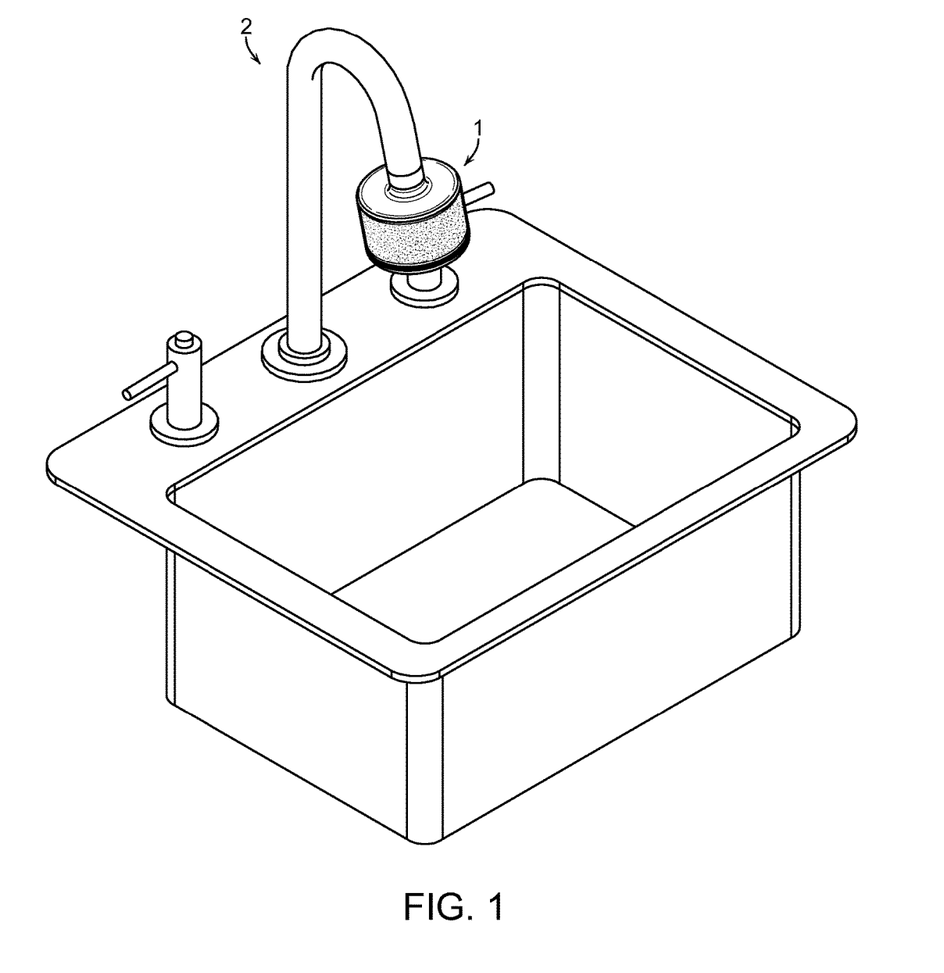
FIG. 1 is a depiction of an embodiment of the device in an exemplary environment of use.
Figure 2:
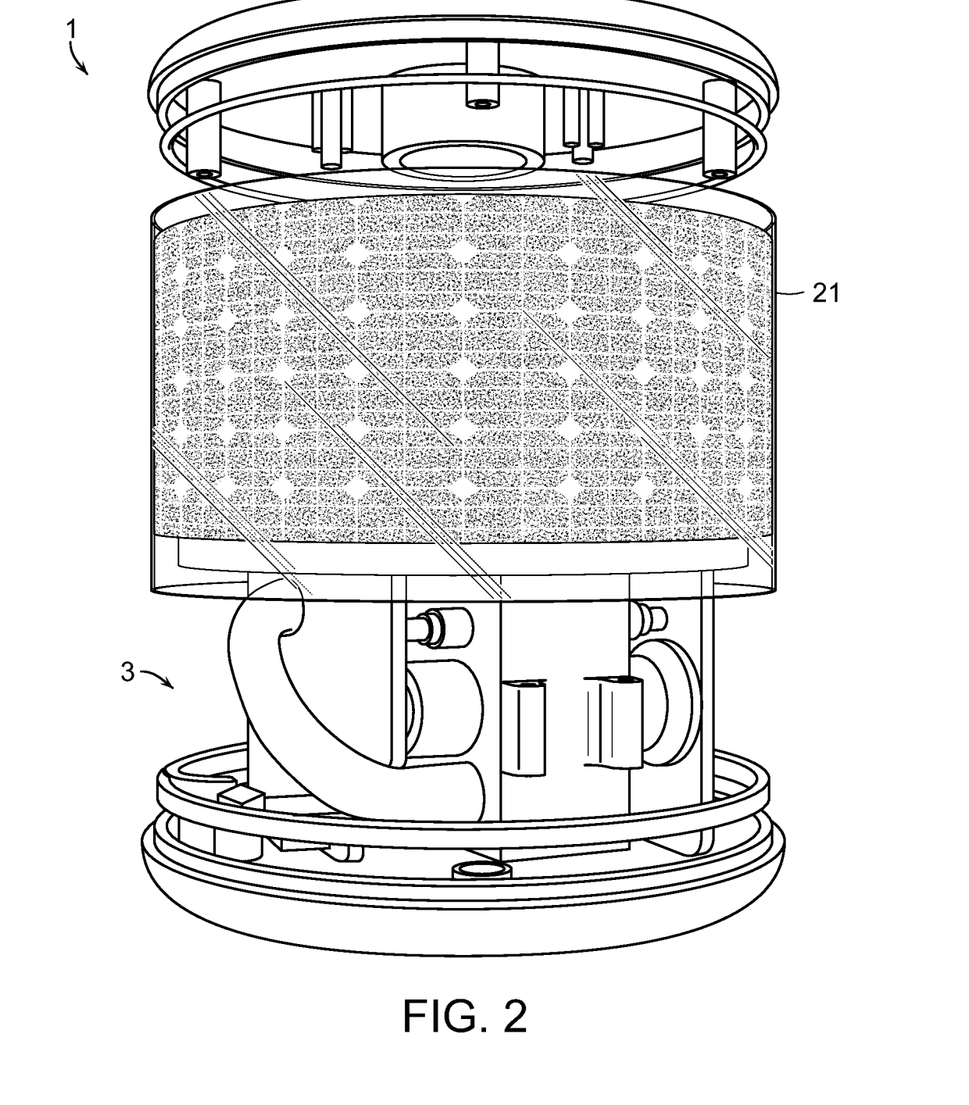
FIG. 2 is a partial expansion of an exemplary embodiment of the device.

Consumers have no means to monitor contaminants in their own residences or commercial spaces. An installable device 1 is described that can be installed directly into a consumer tap 2, as shown by example in FIG. 1. FIG. 2 is an example of how device 1 may be constructed for installation into a tap, with an outer casing 21 enclosing water capture and measurement apparatus 3.

Figure 3:
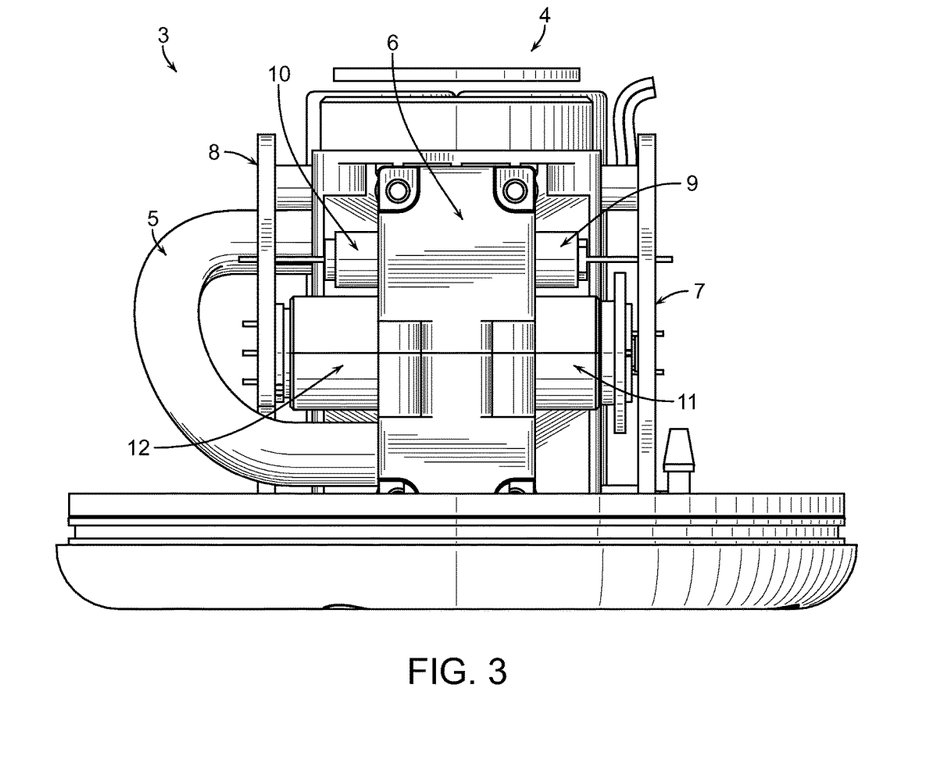
FIG. 3 is a perspective internal view of an exemplary embodiment of the device.
Figure 4:
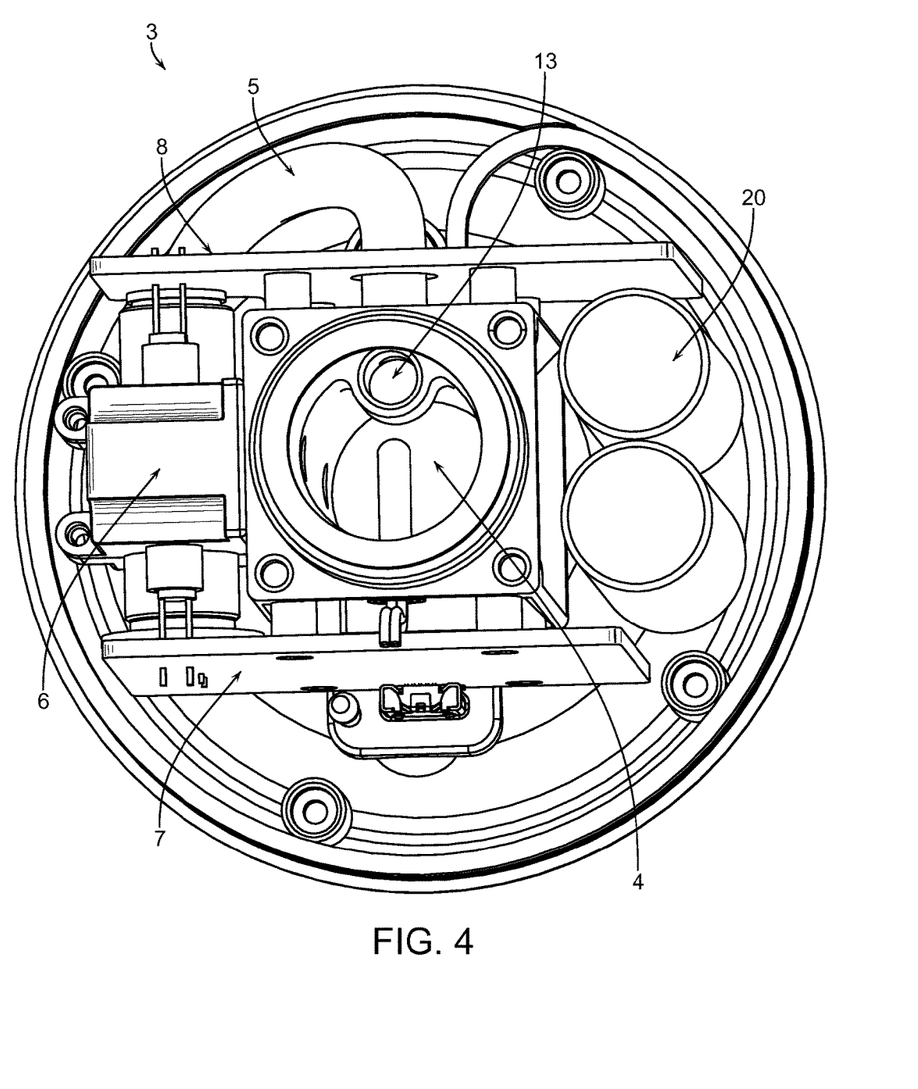
FIG. 4 is a birds-eye, internal view of an exemplary embodiment of the device.

An exemplary apparatus 3 of device 1 will be described with reference to FIGS. 3 and 4. Device 1 is installable into tap 2, such that when the tap is operated, water flows into opening 4. As shown in FIG. 4, most of the water will flow through the opening 4 and out of the tap, but a portion of the flow will enter opening 13 and become diverted through conduit 5.

Chamber 6 receives the diverted fluid from the base of said chamber. In the example presented, water pressure in conduit 5 causes chamber 6 to fill from the base of said chamber. Air bubbles and turbulence, which would typically be associated with a downward waterfall, are reduced within the chamber. This in turn allows one or more receivers to take measurements pertaining to the water in the chamber, and in particular to light measurements that would be affected by turbulence, air and other causes of refraction. Water exits the chamber from the top of the chamber and returns to the flow. It should be noted, however, that alternative examples may utilize a conduit connected to a different section of the chamber, not necessarily the base, so long as one or more receivers is capable of operation. Different structures for diversion of water flow may be desirable to facilitate device installation in different parts of the water line. For instance, a conduit diverting water to the top of the chamber may comprise a buffer to slow the flow of water into the chamber. As another example, the shape of the chamber may facilitate the dissipation of air bubbles, such as by having a large horizontal cross-section at the top.

One or more of the receivers may be a photometric sensor that receives light. As noted above, reduction in turbulence and air in the water greatly facilitates the operation of photometric sensors that receive light passing through the water. The preferred embodiment uses ultraviolet light absorption, preferably at a wavelength of 254 nm (UV254), to correlate with TOC. Ultraviolet wavelengths in the range of 250 to 300 nm are known to be closely correlated to TOC, UV254 having a high adjusted coefficient of determination of 0.997. As depicted in the example, LED 19 outputs UV254, such that receiver 12 measures the amount of UV254 absorbed by fluid within the chamber 6. As is known in the art, chamber 6 may be a quartz cuvette, to facilitate the efficient transmittal of UV254.

Figure 5:
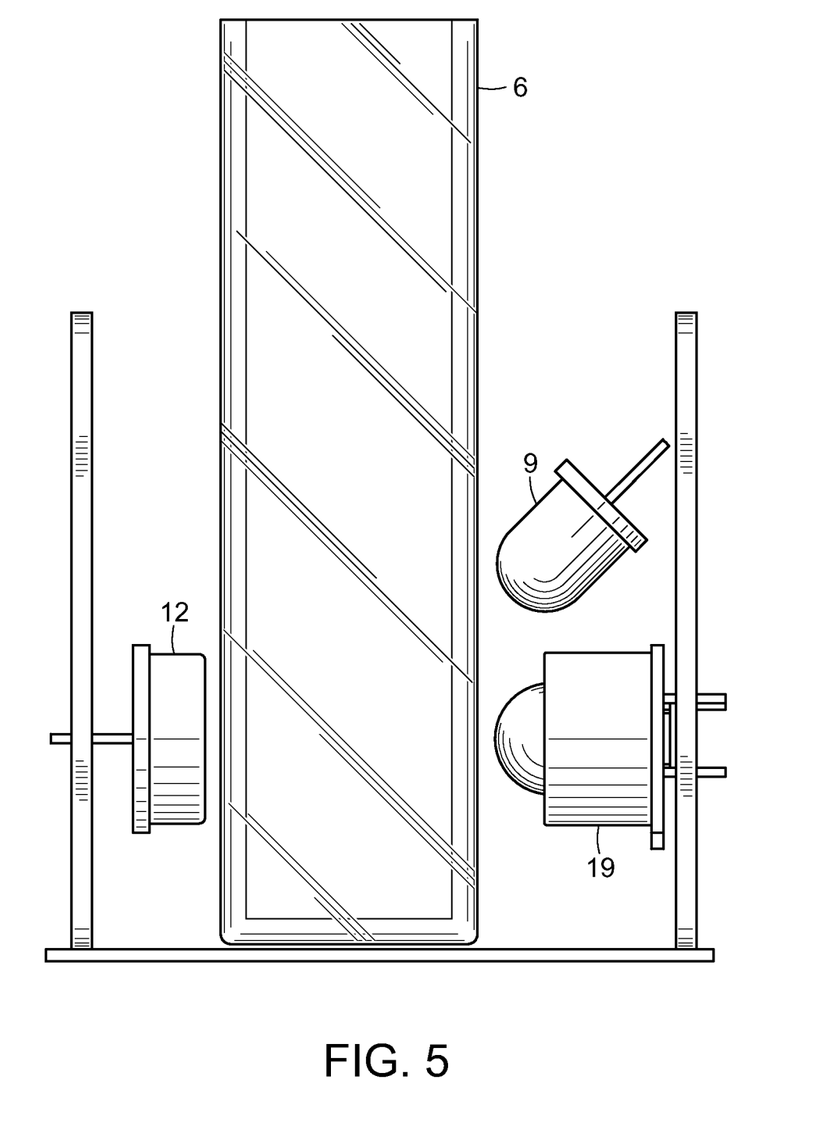
FIG. 5 is a side view showing a chamber and exemplary positions of light sources and receivers in relation to the chamber.

An example of a preferred arrangement for TOC measurement is shown in FIG. 5. Photometric sensor 12 coupled to PCB 8 receives light from UV 254 LED 19, transmitted through quartz cuvette 6. Furthermore, IR (infrared) LED 9 may serve at least two purposes. IR absorption by receiver 12 may be used to calculate turbidity level, which may be of independent interest as contamination, but which may also be used to refine TOC calculation. In addition, by positioning LED 9 at an angle—such as the 45 degree angle depicted by example in FIG. 5—the receiving of light from LED 9 may be used to activate the UV254 LED and/or measurement circuit as follows: light from angled LED 9 will not be received by receiver 12 until the water level in chamber 6 exceeds that of the light source 9, due to refraction. Furthermore, LED 9 being positioned on an indirect path from sensor 12 facilitates the collection of diffused IR only, necessary for turbidity calculation.

Further refinement of TOC calculation can be effected by use of a temperature receiver on or near UV254 LED 19. Data from the temperature receiver can be used to account for diminished UV254 at high temperatures. Thus, TOC in the preferred embodiment may be determined according to the following formula:

$$TOC = K_{toc} * K_{D2*} * D2 * lg(1 - Ka*T)/D1$$

Where $K_{toc}$ is the TOC coefficient, $K_{D2*}$ is the IR turbidity coefficient, D2 is the turbidity ADC measurement, A0 is UV intensity at 0° C., Ka is the UV/temperature intensity coefficient, T is temperature, and D1 is the UV TOC ADC measurement. The TOC coefficient may be adjusted to account for the ultraviolet wavelength actually used.

Figure 6:
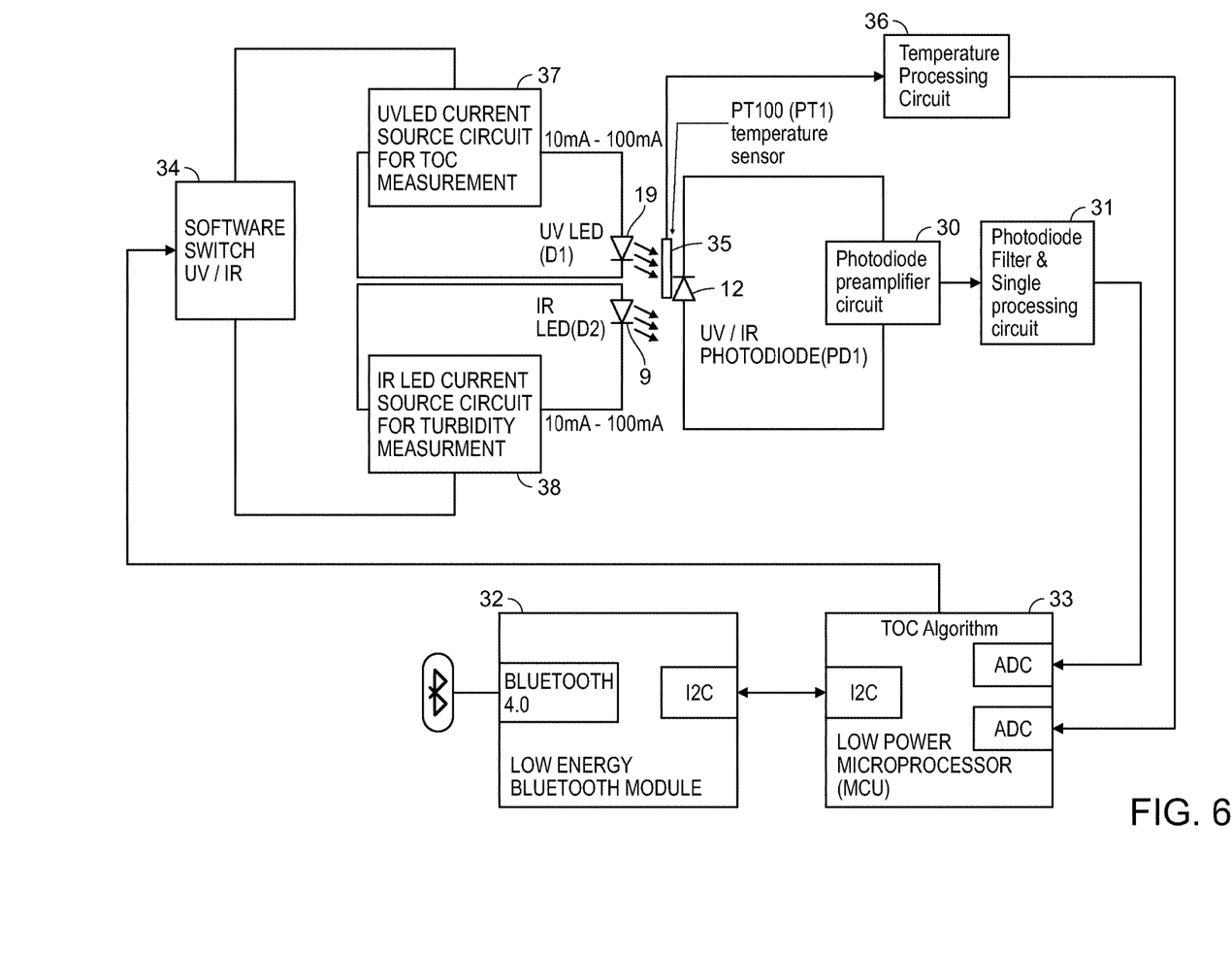
FIG. 6 is an exemplary measurement circuit for the device.

The calculation of TOC may be performed by a measurement circuit, an example of which is shown in FIG. 6. Photodiode 12 capable of receiving UV254 and/or IR transmits current proportional to light absorbed to preamplifier circuit 30. Filter & average and/or additional signal processing may be performed by circuit 31. Furthermore, temperature sensor 35 may transmit temperature near the photodiode to temperature processing circuit 36. UV, IR and temperature data is used to perform the TOC calculation by module 33. As described previously, when chamber 6 has sufficiently filled with water such that IR wavelength from LED 19 can be received by photodiode 12, TOC algorithm module 33 may transmit signal to switch 34 to activate UV254 LED 9, The automatic activation allows the preferred embodiment to require a mere 500 µA of power consumption when the circuit is not activated. Upon activation of UV254 and the TOC measurement circuit, power consumption rises to around 15 mA, but only for the time needed to complete the calculation. Thus, the use of LEDs, automatic activation, high quantum efficiency photodiodes, and accurate signal processing each contribute to the low power consumption of the device.

Power may be delivered by any means, including by battery pack 20 as depicted, or any other means including, but not limited to, AC/DC, solar and hydroelectric power. The low power requirement of the device enables the use of low power sources such as solar. Solar panels may be located directly on the outer casing 21. The battery pack may be removable, replaceable, and/or rechargeable by USB or a wall outlet connection.

Other embodiments of the device may comprise any combination and types of receivers. The positioning of receivers depicted in the drawings is exemplary, and receivers may be located anywhere on, near or in the chamber. Receivers may be any type of receivers currently known in the art, including, but not limited to, photometric sensors for receiving light, temperature probes for determining temperature, and electrodes for measuring resistance. For instance, Total Dissolved Solids (TDS), known to be correlated to conductivity, may be measured by determining the resistance between two electrodes within the sample chamber. Similarly, the voltage between an electrode within water in the sample chamber and another electrode within a fixed pH liquid, may be used to determine pH of the water.

Figure 7:
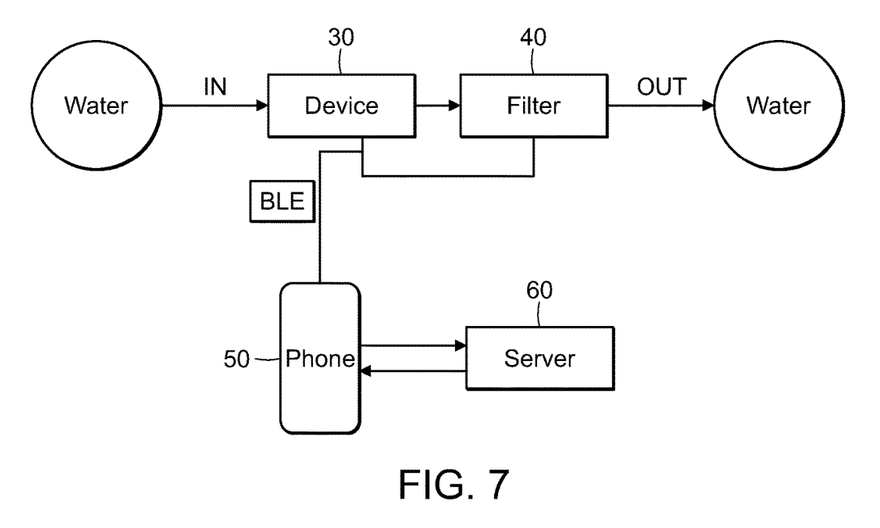
FIG. 7 is a system schematic of the device operable to send data to a remote apparatus such as a phone.

As shown by example in FIG. 6, the device may comprise a low-power Bluetooth module 32 to transmit contamination information to a remote device. FIG. 7 is a schematic showing the device 3 in Bluetooth or other wireless connection to smartphone 50. Smartphone device 50 may also be capable of sending and receiving data to server 60 for the collection and management of user water contamination data. The display of contamination information need not be remote, however, indeed may be anywhere on the device itself, such as on the outer casing 21.

Figure 8:
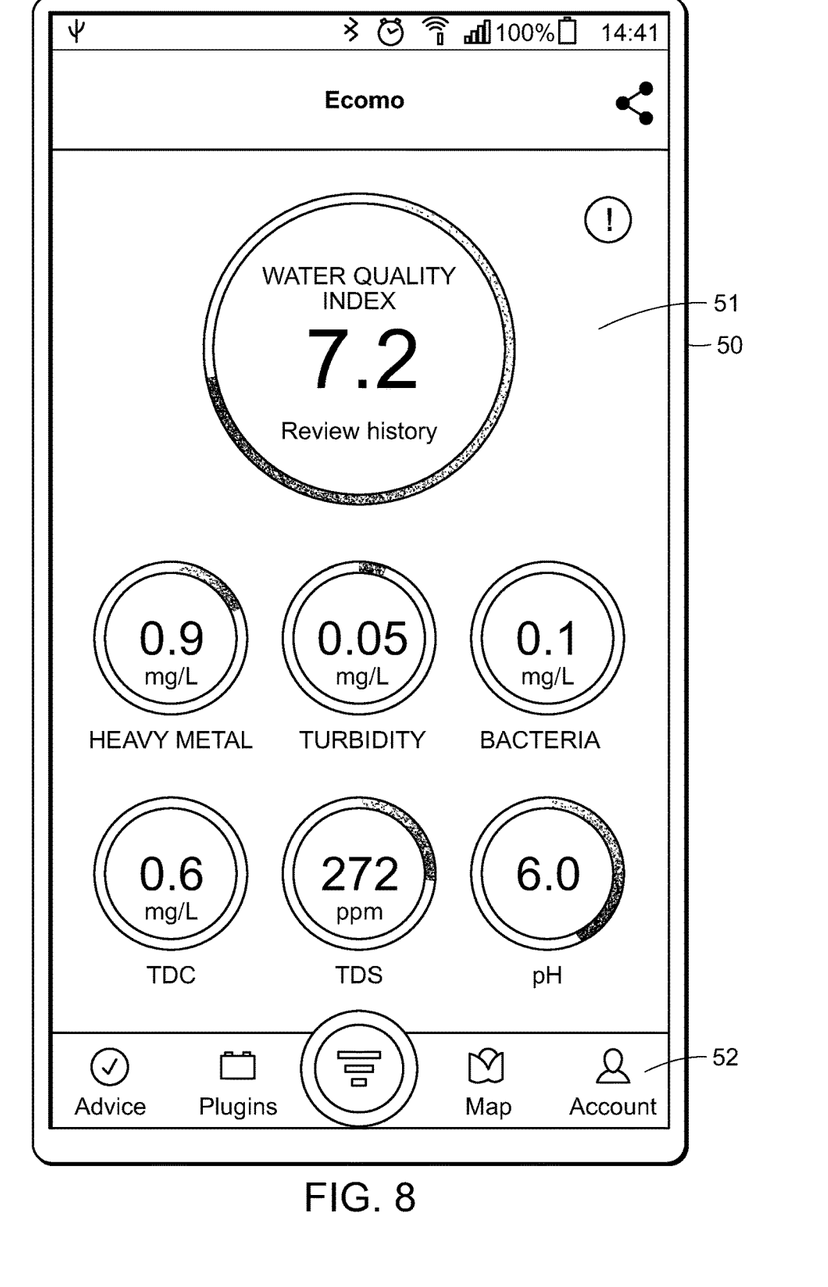
FIG. 8 is a sample remote apparatus displaying data received from the device.

The described device enables the collection of a variety of contamination data, which can be transmitted and processed according to methods widely known in the art. For instance, FIG. 8 shows a display screen 51 on user device 50, the display screen showing current levels of heavy metals, turbidity, bacteria, TOC, TDS and PH that has been transmitted from device 3.

To further illustrate uses of the device, a water filter 40 may be connectable to the device to improve water quality. Thus, when water quality at a tap diminishes and its user is made aware by the device or remote display 51, the user may desire to install a new water filter, a choice that may be made directly from user's device.

The invention claimed is:

1. An apparatus for installation onto a fluid pipe that is operable by a tap, the apparatus comprising:
    a chamber that receives a portion of fluid flow diverted from the fluid pipe;
    a conduit that receives a flow of fluid from the fluid pipe and diverts the portion of fluid flow to the chamber, wherein operation of the tap causes the chamber to fill with the portion of fluid flow diverted to the chamber and drain back to the flow;
    at least one photometric sensor for measuring the amount of light absorbed by the fluid within the chamber;
    an ultraviolet light emitting diode that, when the chamber is full, is activated to emit light to the chamber such that the at least one photometric sensor measures the amount of ultraviolet light absorbed by the fluid within the chamber; and
    a circuit configured to convert ultraviolet light absorbance from the photometric sensor to generate a signal for transmitting contaminant data.

2. The apparatus of claim 1 wherein the flow of fluid in the conduit pushes fluid into the base of the chamber to fill the chamber.

3. The apparatus of claim 1 wherein the ultraviolet light emitting diode is activated in response to the photometric sensor light from a second light emitting diode.

4. A process comprising:
    diverting a portion of a flow of fluid off of a fluid pipe, through a conduit, and into a chamber,
    receiving, by at least one photometric sensor, a measurement of the amount of light absorbed by fluid diverted into the chamber; and
    sending fluid out of the chamber back to the flow of fluid,
    wherein, when the chamber is full, the photometric sensor receives light from an ultraviolet light emitting diode that is activated to emit light to the chamber such that the at least one photometric sensor measures the amount of ultraviolet light absorbed by the fluid within the chamber and sends said measurement to a circuit configured to convert ultraviolet light absorbance from the photometric sensor to generate a signal for transmitting contaminant data.

5. The process of claim 4 wherein the flow of fluid in the conduit pushes fluid into the base of the chamber to fill the chamber.

6. The process of claim 4 wherein the ultraviolet light emitting diode is activated in response to the photometric sensor receiving light from a second light emitting diode.

7. An apparatus for monitoring contamination in a fluid pipe that is operable by a tap, the apparatus operable to receive contamination data from a device installed into the fluid pipe, the device comprising:
    a chamber that receives a portion of fluid flow diverted from the fluid pipe;
    a conduit that receives a flow of fluid from the fluid pipe and diverts the portion of fluid flow to the chamber, wherein operation of the tap causes the chamber to fill with the portion of fluid flow diverted to the chamber and drain back to the flow;
    at least one photometric sensor for measuring the amount of light absorbed by fluid within the chamber;
    an ultraviolet light emitting diode that, when the chamber is full, is activated to emit light to the chamber such that the at least one photometric sensor measures the amount of ultraviolet light absorbed by the fluid within the chamber; and
    a circuit configured to convert ultraviolet light absorbance from the photometric sensor to generate a signal for transmitting contaminant data.

8. The apparatus of claim 7 wherein the flow of fluid in the conduit pushes fluid into the base of the chamber to fill the chamber.

9. The apparatus of claim 7 wherein the ultraviolet light emitting diode is activated in response to photometric sensor receiving light from a second light emitting diode.

* * * * *